United States Patent [19]

Matson et al.

[11] Patent Number: 5,062,423
[45] Date of Patent: Nov. 5, 1991

[54] EQUINE AEROSOL DRUG DELIVERY METHOD AND APPARATUS

[75] Inventors: Charles J. Matson; David J. Velasquez, both of St. Paul, Minn.

[73] Assignee: Minnesota Mining and Manufacturing Company, St. Paul, Minn.

[21] Appl. No.: 486,609

[22] Filed: Feb. 27, 1990

[51] Int. Cl.$^5$ .................... A61M 16/00; A61M 15/00; A61M 11/00; A62B 7/00
[52] U.S. Cl. .......................... 128/207.15; 128/203.12; 128/200.23; 128/205.23
[58] Field of Search ............... 128/204.18, 203.12, 128/207.18, 200.23, 204.26, 205.23, 202.22, 207.15

[56] References Cited

U.S. PATENT DOCUMENTS

| | | | |
|---|---|---|---|
| 440,713 | 11/1890 | Krohne et al. | 128/205.23 |
| 2,843,119 | 7/1958 | Glasser | 128/142 |
| 3,312,744 | 11/1962 | Brunet et al. | 222/402.2 |
| 3,456,646 | 7/1969 | Phillips et al. | 128/173 |
| 3,628,532 | 12/1971 | Magrath | 128/145.8 |
| 3,738,542 | 6/1973 | Ruscitti | 222/402.16 |
| 3,881,479 | 5/1975 | Carden | 128/DIG. 26 |
| 3,915,165 | 10/1975 | Rambosek et al. | 128/145.8 |
| 4,143,658 | 3/1979 | Rambosek et al. | 128/184 |
| 4,186,737 | 2/1980 | Valenta et al. | 128/203.28 |
| 4,192,860 | 3/1980 | Griffiths | 424/43 |
| 4,270,530 | 6/1981 | Baum et al. | 128/204.25 |
| 4,327,721 | 5/1982 | Goldin et al. | 128/207.15 |
| 4,343,304 | 8/1982 | Hickmann | 128/200.14 |
| 4,396,015 | 8/1983 | Johnson | 128/200.14 |
| 4,407,481 | 10/1983 | Bolton et al. | 251/353 |
| 4,452,241 | 6/1984 | Sarnoff et al. | 128/204.18 |
| 4,484,577 | 11/1984 | Sakner et al. | 128/203.28 |
| 4,519,388 | 5/1985 | Schwanbom et al. | 128/204.25 |
| 4,534,343 | 8/1985 | Nowacki et al. | 128/200.23 |
| 4,546,768 | 10/1985 | Ferierabend | 128/200.16 |
| 4,584,997 | 4/1986 | Delong | 128/205.23 |
| 4,644,947 | 2/1987 | Whitwam et al. | 128/204.25 |
| 4,664,107 | 5/1987 | Wass | 128/200.23 |
| 4,669,463 | 6/1987 | McConnell | 128/207.14 |
| 4,722,334 | 2/1988 | Blackmer et al. | 128/203.16 |
| 4,790,305 | 12/1988 | Zoltan et al. | 128/200.23 |
| 4,819,834 | 4/1989 | Theil | 222/355 |
| 4,938,210 | 7/1990 | Shene | 128/203.12 |
| 4,953,546 | 9/1990 | Blackmer et al. | 128/203.16 |
| 4,960,122 | 10/1990 | Mizus | 128/207.14 |
| 4,977,894 | 12/1990 | Davies | 128/207.15 |

FOREIGN PATENT DOCUMENTS 0245607 3/1987 European Pat. Off. .
89/05670 6/1989 PCT Int'l Appl. .
2111838 7/1983 United Kingdom .

OTHER PUBLICATIONS

Safety of Intratracheal Spray (ITS) of Kanamycin Applied to Calves Sonoda, M., et al., (College of Dairying, Dairy Science), Journal of the Veterinary Medicine, No. 819 (1989) pp. 647-651 (English Translation).
EPO Search Report.
English Translation of Package Insert for Product Known as "Intratrachael Jet Kanamycin Toyo" and a Package Descr. of Associated Catheter pp. 1-5.
Ichioka, T. et al., "Adsorption Distribution and Residue of Kanamycin Administered by Endotracheal Spraying in Calves", Jour. of Vet. Med. (1989), No. 812 pp. 168-172.

(List continued on next page.)

Primary Examiner—Edgar S. Burr
Assistant Examiner—Kimberly L. Asher
Attorney, Agent, or Firm—Gary L. Griswold; Walter N. Kirn; Jeffrey J. Hohenshell

[57] ABSTRACT

A method of and apparatus for delivering a dose of an aerosol drug to the lungs of a large animal, such as a horse. A distal end of an endotracheal-like nasal tube is inserted through a nostril of the large animal into its nasal-pharyngeal cavity. Then, as air flows inwardly through the lumen of the nasal tube toward the lungs of the large animal, an atomized aerosol drug dose is discharged into the lumen of the nasal tube. The inwardly-flowing air carries the atomized drug dose with it for delivery to the lungs of the large animal.

20 Claims, 4 Drawing Sheets

OTHER PUBLICATIONS

Sonoda et al., "Safety of Intratracheal Spray (ITS) of Kanamycin Applied to Calves" Journal of Vet. Med., No. 819 (1989) pp. 647–651.

Ogata, Y. et al., "Therapeutic Effects of Intratracheal Atomized Kanamycin on Enzootic Pneumonia in Calves", Jour. of Vet. Medicine, No. 818 (1989) pp. 49–52.

Ogata, "Intratracheal Spraying Therapy to Pneumonia of Calves", Journal of Clinical Veterinary Medicine, vol. 8, No. 4 (1990), pp. 35–37.

Airway Reactivity in Ponies with Recurrent Airway Obstruction (heaves), F. J. Dirksen et al., Journal of Applied Physiology 58(2). 598–604 (1985).

Emergency Endotracheal Drug Administration Using Aerosol; D. J. Steedman et al. Resuscitation 15:135–139 (Ireland 1987).

Aerosol Delivery in Intubated, Mechanically Ventilated Patients; MacIntyre et al. Critical Care Medicine, 13:81–84 (Feb. 1985).

M. J. Diamon, Letter to Editor; "Delivering Bronchodilators into the Anesthesia Circuit: Anesthesiology" 64:531 (Apr. 1986).

Model #9056 Bronchodilator Tee; Boehringer Laboratories Inc. Wynnewood, Penn. Cart Frame 9055–482.

"Flowmeters and Sight Flow Indicators" Dwyer Instruments, Inc. (1984).

Summary of Toyojozo to Market Device for Treatment of Pneumonia.

EQUINE AEROSOL DRUG DELIVERY METHOD AND APPARATUS

This invention relates generally to drug delivery methods and apparatus, and more particularly to a method and apparatus for delivering an atomized aerosol drug dose to the lungs of a large animal, such as a horse, to treat various conditions or ailments, such as recurrent airway obstruction or heaves.

BACKGROUND OF THE INVENTION

Large animals, such as horses and many farm animals, frequently develop heaves and/or pulmonary hemorrhage. Heaves, like asthma, is characterized by acute airway obstruction. Pulmonary hemorrhage occurs when the capillaries within the lung rupture or become abnormally permeable, which allows blood to enter the airways. In either case, the resulting bronchoconstrictive state can cause the animal to become hypoxic (i.e., to have a subnormal oxygen level in the blood).

Heaves is found among barnyard animals exposed to hay (see, e.g., F.J. Dirksen et al., Airway Reactivity in Ponies with Recurrent Airway Obstruction (Heaves), Journal of Applied Physiology 58(2): 598-604 (1985)). Heaves in horses has been treated by injecting relatively large doses of medication directly into the blood stream of the horse. Large doses are required since the medication has not been specifically targeted to the lungs of the animal, with the increased risk of undesirable side effects that large doses may cause.

Strenuous exercise, such as racing, can initiate a bronchoconstrictive state that may lead to pulmonary hemorrhage. During strenuous exercise, the capillaries within the lung may rupture or become abnormally permeable, allowing blood to enter the airways and reducing the respiratory capacity of the lungs. In many thoroughbred race horses, the pulmonary hemorrhage has been so severe that the horse becomes of marginal economic value on the racing circuit or as a breeder. These horses are commonly classified as "bleeders".

Diuretics have been employed to attentuate pulmonary hemorrhage. When it is approved by a race track, the prophylactic method of choice has been to inject the diuretic furosemide sold under the trade designation "Lasix" by Hoechst-Roussel Pharmaceuticals, Inc. of Somerville, New Jersey, U.S.A. Diuretics can reduce or prevent such hemorrhage by depleting water and electrolyte in the blood stream to reduce blood pressure.

U.S Pat. Nos. 3,915,165 and 4,143,658 describe intratracheal injection systems for injecting dry medicaments in a gaseous suspension into the trachea of an animal in order to treat pneumonia. That system includes needle means (e.g., catheter) that is inserted into the trachea of the animal by puncturing the catheter/needle through tracheal tissue between consecutive cartilage rings thereof. The dry medicaments are administered through the catheter.

The Toyojozo Co., Ltd., of Tokyo, Japan has reportedly developed a device for treating pneumonia in calves. The device apparently consists of a catheter connected to an aerosol canister containing the aminoglycoside antibiotic kanamycin sulfate and using carbon dioxide as a propellant. Use of that device reportedly involves tracheal cannulation of the catheter via the nasal passage, followed by direct administration of atomized drug into the calf's lungs.

The methods described above share at least one common disadvantage in that they are not specifically adapted for regular prophylactic use. Injections, tracheotomies and tracheal cannulation or intubation are difficult, painful and generally undesirable procedures to perform repeatedly in order to prevent bronchoconstriction or pulmonary hemorrhage.

SUMMARY OF THE INVENTION

This invention provides a method and apparatus for delivering a dose of an aerosol drug (e.g., a bronchodilator) to the lungs of a large animal, such as a horse. The method and apparatus are particularly designed for treating various conditions or ailments, such as recurrent airway obstruction or pulmonary hemorrhage, which may be most effectively treated via the respiratory system of the animal. The invention permits smaller doses of the drug in order to provide effective treatment than would injection of the drug into the circulatory system, and is adapted for use in treating unsedated large animals. The method is designed to be useful as a regular prophylactic treatment, without tracheal intubation.

Generally, the method of the invention involves inserting a distal end of an endotracheal-like nasal tube through a nostril and nasal cavity of the large animal until the distal end of the tube is positioned within the nasal-pharyngeal cavity of the animal. This is done in such a manner that a lumen of the nasal tube communicates with the lungs of the large animal. As air flows inwardly through the lumen of the nasal tube toward the lungs, an atomized aerosol drug dose is discharged into the lumen of the nasal tube for delivery of the atomized drug dose to the lungs of the large animal.

Preferably, air flow through the lumen of the nasal tube is determined so that the atomized drug dose may be discharged during the onset of inspiratory air flow through the lumen of the nasal tube toward the lungs of the large animal. For example, an air flow indicator may be provided including a vane movable in response to air flow through the lumen of the nasal tube, and the onset of air flow through the lumen may be determined by observing movement of the vane.

Generally, the apparatus of the invention is adapted for use with a canister of the type for dispensing a metered dose of a drug through a hollow stem when the stem is actuated. The apparatus comprises an endotracheal-like nasal tube and an aerosol-generating device. The nasal tube has proximal and distal ends, a lumen extending between the proximal and distal ends, and a length and width appropriate for insertion of the distal end of the nasal tube through a nostril and nasal cavity of the large animal into the nasal-pharyngeal cavity of the large animal.

The aerosol-generating device is mounted on the proximal end of the nasal tube, and comprises a body having an air passageway communicating with the lumen of the nasal tube and an air opening opposite the nasal tube. A stem receptacle is provided outside and generally adjacent the air passageway for receiving the stem of the canister. The stem is moved toward the canister when the canister is pushed toward the stem receptacle so that the stem may be actuated. A hollow tube extends generally transversely across the air passageway, and communicates with a hollow stem in the stem receptacle. The hollow tube has an orifice opening into the air passageway for delivering an atomized aerosol dose to the air passageway for administration through the nasal tube to the lungs of the large animal.

Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF A PREFERRED EMBODIMENT

Figure 1:
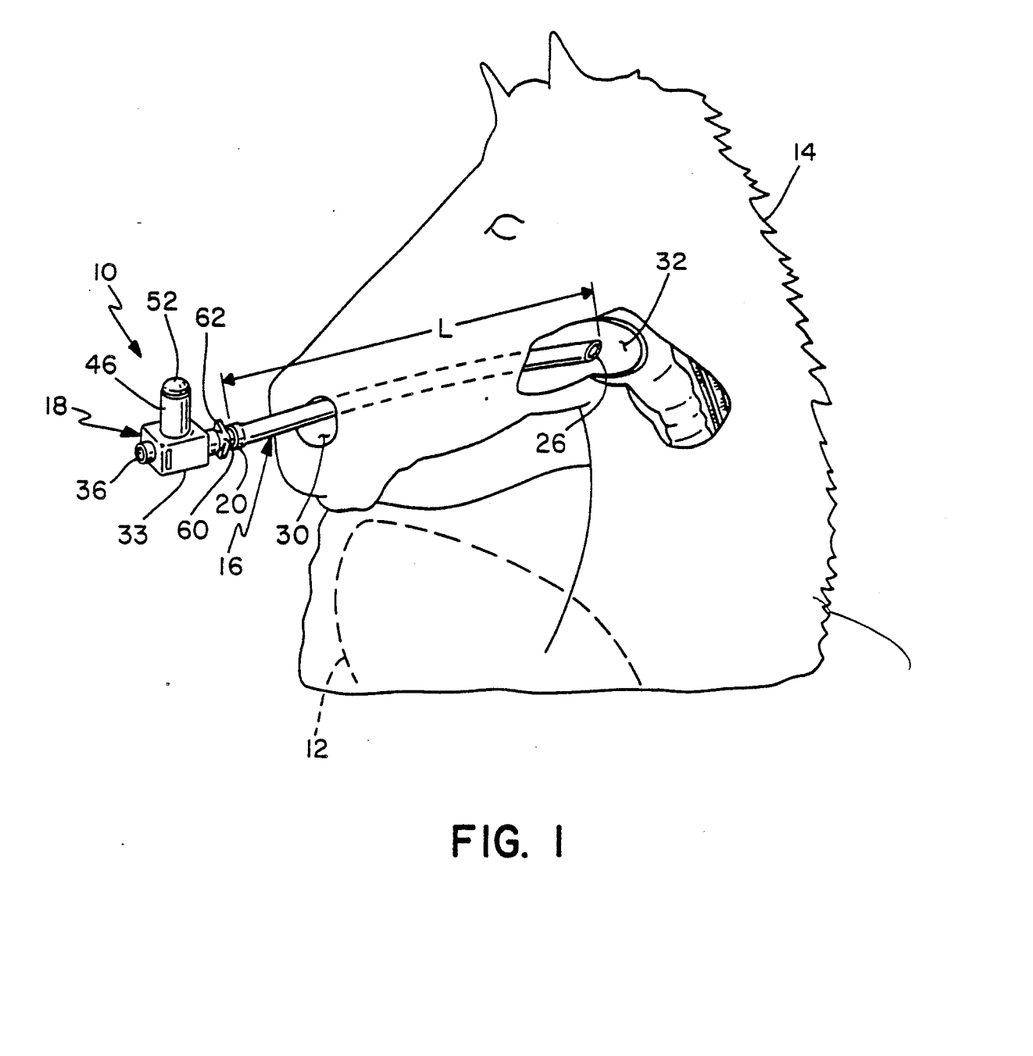
FIG. 1 is a side view of the upper, forward region of a horse being treated according to the invention, with portions being broken away to illustrate placement of an apparatus used in practicing the invention.

Now referring to the drawing, the apparatus of the invention is designated in its entirety by the reference numeral 10. As illustrated in FIG. 1, the method and apparatus 10 of the invention are useful for delivering a metered dose of an aerosol drug to the lungs 12 of a large animal, such as a horse 14.

The apparatus 10 generally comprises an elongate endotracheal-like nasal tube 16, and an aerosol-generating device 18 removably mounted on the proximal end 20 of the endotracheal-like tube 16. As used herein, "endotracheal-like" refers to tubing of the general type of endotracheal tubes, but is not intended to be limited to tubing that is actually positioned within the trachea of the animal.

The aerosol-generating device 18 is adapted for use with a canister 22 of the type for dispensing a metered dose of a drug through a hollow stem 24. A metered dose is dispensed from such a canister 22 when a metering valve mechanism (not shown) is actuated, which typically occurs when the stem 24 is moved toward the canister 22. For example, suitable canisters 22 are described in U.S. Pat. Nos. 4,819,834 and 3,738,542 (incorporated herein by reference). Canisters 22 of this type include a propellant and multiple doses of the drug, which are discharged in predetermined standard amounts via a metering valve mechanism (not shown) actuated either by inward movement of the stem 24, or outward movement of the stem 24 following inward movement. Such metering valve mechanisms are typically designed to deliver a predetermined volume of the aerosol dose, for example, 50 or 63 microliters, each time the mechanism is actuated.

The nasal tube 16 has proximal and distal ends 20 and 26, and a lumen 28 extending between the proximal and distal ends. The length L and width W of the nasal tube 16 are appropriate for insertion of the distal end 26 of the nasal tube 16 through a nostril 30 and nasal cavity of the large animal 14 into the nasal-pharyngeal cavity 32. For example, the nasal tube 16 may be generally cylindrical, and have an inner diameter of approximately 9 mm, an outer diameter W of approximately 12 mm, and a length L of approximately 350 mm.

The distal end 26 of the nasal tube 16 is preferably tapered or offset at an angle (e.g., approximately 40 degrees) with respect to the central longitudinal axis of the tube 16 and the edge 26 of the tube forming the distal end 26 is smoothly rounded in order to facilitate introducing the nasal tube 16 into the nostril 30 and nasal-pharyngeal cavity 32 of the animal 14.

The nasal tube 16 is generally flexible, but has sufficient rigidity to facilitate introducing the tube 16 into the nasal cavity of the animal 14. Suitable materials for the nasal tube 16 include various medical grade polymeric materials, such as polypropylene or silastic.

Figure 2:
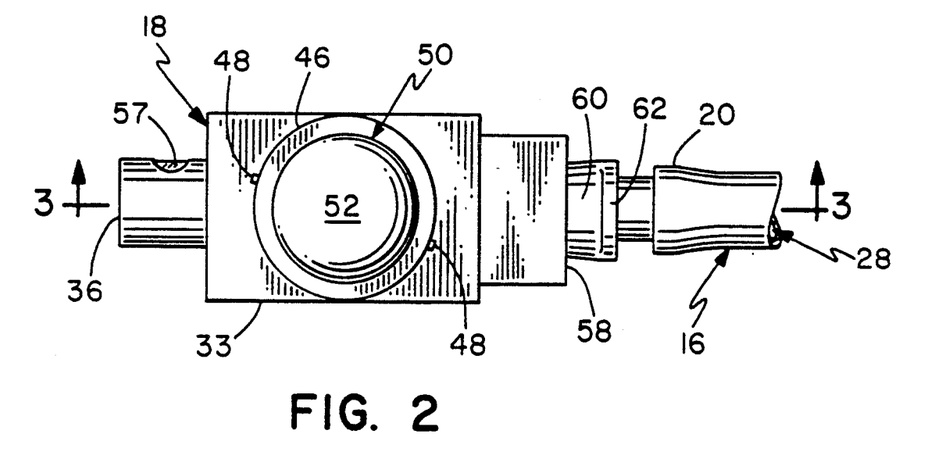
FIG. 2 is an enlarged top plan view of an aerosol-generating device of the apparatus of FIG. 1.
Figure 3:
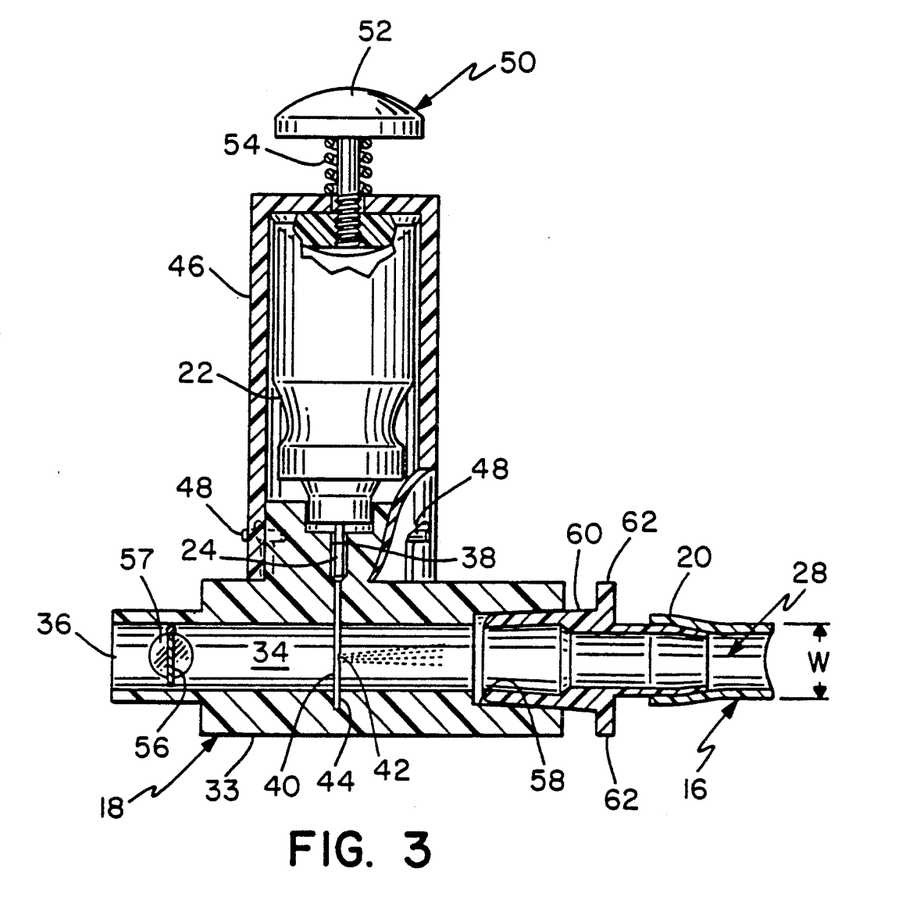
FIG. 3 is a cross-sectional view substantially along line 3—3 of FIG. 2.
Figure 4:
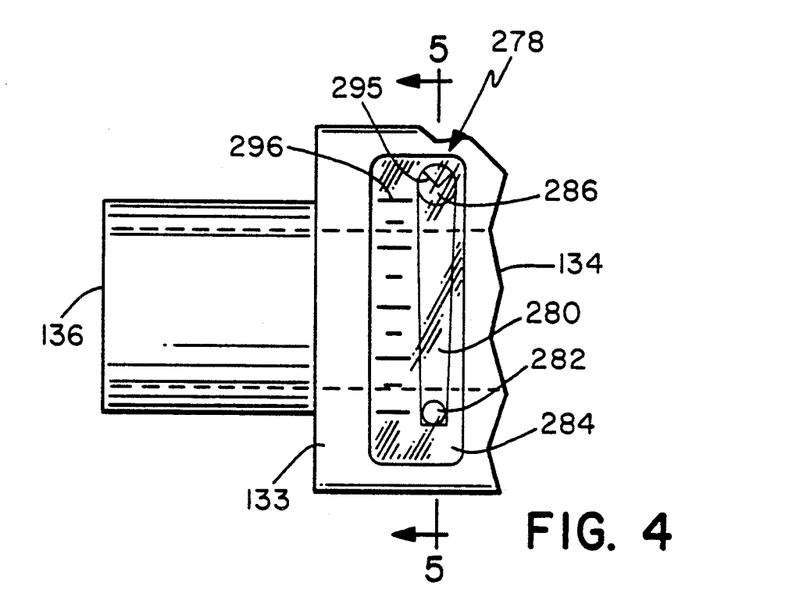
FIG. 4 is a side view of a portion of an aerosol-generating device similar in many respects to the aerosol-generating device of FIGS. 1-3, illustrating an alternative embodiment of an air flow indicator of the invention.
Figure 5:
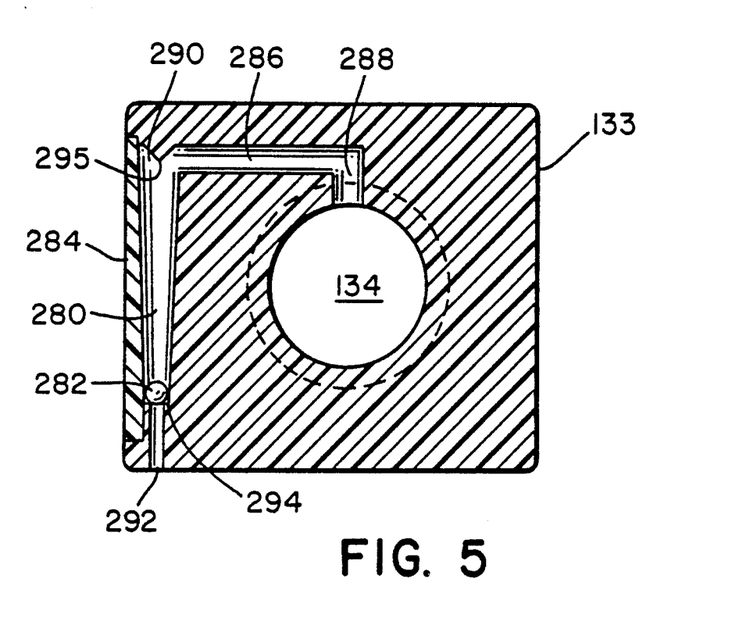
FIG. 5 is a cross-sectional view along substantially along line 5—5 of FIG. 4.

The aerosol-generating device 18 comprises a body 33 having an air passageway 34 communicating with the lumen 28 of the nasal tube 16 and an air opening 36 opposite the nasal tube 16. A stem receptacle 38 is provided in the body 33 outside and generally adjacent the air passageway 34 for receiving the stem 24 of the canister 22. A hollow tube 40 extends generally transversely or laterally across the air passageway 34 from a portion of the wall of the passageway 34 adjacent the stem receptacle 38. As used herein, "transversely" or "laterally" refers to the arrangement, for example, of the hollow tube 40 with its longitudinal axis in a generally perpendicular orientation with respect to the central longitudinal axis of the air passageway 34.

The hollow tube 40 is in fluid communication with a hollow stem 24 received in the stem receptacle 38, and the stem receptacle 38 seals along the sides of the stem 24 so that a metered dose discharged from the canister 22 is forced into the hollow tube 40. The arrangement is such that, when the canister 22 is pushed toward the stem receptacle 38, the stem 24 is moved toward the canister 22 to actuate the metering valve mechanism and discharge a dose into the hollow tube 40.

An orifice 42 is provided in the hollow tube 40, and opens into the air passageway 34 from the bore of the tube 40 for atomizing and delivering a metered aerosol dose into the air stream flowing through the air passageway 34. The orifice 42 preferably opens through the hollow tube 40 along the central longitudinal axis of the air passageway 34 in the direction toward the nasal tube 16 (rightwardly in FIG. 3) to facilitate entraining the aerosol medication in the air stream, while minimizing the amount of medication deposited along the walls of the air passageway 34 of the aerosol-generating device 18. Most preferably, the hollow tube 40 extends completely across the air passageway 34 and the orifice 42 is positioned along the midpoint of the hollow tube 40. The portion of the hollow tube 40 between the orifice 42 and the lower embedded end 44 may either be hollow or filled.

The hollow tube 40 may be formed of a narrow stainless steel tube (also 40) having an outside diameter of approximately 0.049 in. (1.2 mm), and an inside diameter of approximately 0.033 in. (0.81 mm), which is appropriate for preventing premature atomization of a metered dose inside the hollow tube 40. The length of the hollow tube 40 is preferably sufficiently greater than the inside diameter of the air passageway 34 to permit both ends of the hollow tube 40 to be embedded in the walls forming the air passageway 34. The orifice 42 preferably has a circular cross section of approximately 23 thousands of an inch (584 micrometers) diameter.

Figure 6:
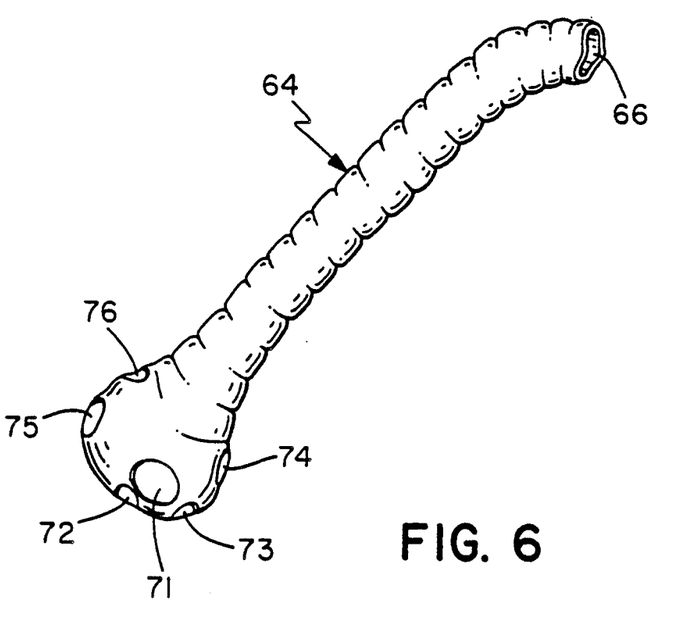
FIG. 6 is a longitudinal view of an excised horse trachea illustrating various locations where the dispersion of a drug administered by the apparatus has been measured.

A canister housing 46 may be provided for securing canisters 22 for operation of the aerosol-generating device 18. The canister housing 46 is detachably mountable on the body 33 of the aerosol-generating device 18 via, for example, a bayonet fastening mechanism illustrated generally at 48.

A triggering mechanism 50 may also be provided for moving the canister 22 toward the stem receptacle 38, thereby moving the stem 24 of the canister 22 toward the canister 22 to actuate the metering valve mechanism and discharge an aerosol dose into the hollow tube 40. For example, the triggering mechanism 50 may be of the type illustrated in FIG. 3, which includes a push button 52 for releasably pressing the canister 22 toward the stem receptacle 38 to discharge a metered dose, and a resilient coil spring 54 pressing against both the push button 52 and the housing 46 to bias the push button 52 toward its ready position (not shown but upwardly from the position shown in FIG. 3).

An air flow indicator is preferably mounted in the air passageway 34 of the body 33 to visibly or audibly indicate when a metered dose should be discharged from the canister 22 for optimum effect. For example, the indicator may include a vane 56 (FIG. 3) movable (pivotable) in response to air flow through the lumen 28 of the nasal tube 16. A window 57 may be provided in the body 33 of the aerosol-generating device 18 so that the vane 56 may be observed visibly. Such a vane 56 may readily be adapted to generate an audible signal by striking the wall of the air passageway 34 when reduced pressure causes it to pivot. The vane 56 may be operatively linked with a visible indicating needle (not shown) to indicate when a metered dose should be discharged.

FIGS. 4 and 5 illustrate an alternative embodiment of an air flow indicator 278 utilizing the characteristic of gas pressure dropping as the velocity of gas flow through the air passageway 134 increases. (Three digit reference numerals beginning with the digit "1" in FIGS. 4 and 5 refer to features corresponding generally to the features indicated in the other figures by reference numerals identical to the last two digits. Three digit reference numerals beginning with the digit "2" refer to features shown only in FIGS. 4 and 5.) As shown in FIG. 5, the air flow indicator 278 includes a frustoconical or tapered passageway 280 communicating with the air passageway 134 and ambient air, and a float ball 282 movable in the tapered passageway 280 in response to air flow induced by reduced pressure in the air passageway 134. Air flow through the air passageway 134 is determined by observing the position of the float ball 282 through the transparent walls of the air indicating window or portion 284 formed in the body 133.

Most preferably, the air flow indicator 278 includes horizontal and vertical passageways 286 and 288 providing fluid communication between the upper end 290 of the tapered passageway 280 and an upper portion of the air passageway 134, and a vent 292 providing fluid communication between the bottom end 294 of the tapered passageway 280 and ambient air. The tapered passageway 280 is tapered inwardly toward its bottom end 294 so that an increasing amount of air flow upwardly through the tapered passageway 280 is required to move the float ball 282 upwardly in the tapered passageway 280. A float stop 295 is provided adjacent the upper end 290 of the tapered bore 280 and the horizontal passageway 286 to prevent the float ball 282 entering the horizontal passageway 286.

Indicia 296 may be provided on or adjacent the window 284 to indicate the amount of flow through the air passageway 134 corresponding to the position of the float ball 282. The taper and length of the tapered passageway 280 control the sensitivity of the indicator 278 and the range of air velocities that may be measured. Sensitivity of the indicator 278 is higher when the taper is shallow (i.e., with a small angle of taper), but the measuring range is less (assuming a constant length). Of course, the measuring range is greater when the tapered passageway 280 is longer.

The bore forming the air passageway 34 is preferably tapered and of increased diameter adjacent the (outlet) end of the air passageway 34, which is opposite the air (inlet) opening 36, to form a tapered mounting section 58. The proximal end 20 of the nasal tube 16 includes a corresponding tapered fitting 60 which is slidably received in the tapered mounting section 58. The tapered fitting 60 and tapered mounting section 58 are tapered at a "self-locking angle" (i.e., tapered at an angle where the fitting 60 and section 58 tend to wedge together securely when pushed together). The mounting section 58 is tapered inwardly in the direction toward the hollow tube 40 (leftwardly in FIG. 3), and the fitting 60 is tapered inwardly in the proximal direction (leftwardly in FIG. 3). The mounting section 58 constitutes one illustrative design of a tube-connecting means, although other types of connections are also contemplated.

Outwardly-extending flanges 62 are preferably provided on the tapered fitting 60 to provide a suitable place for manually gripping the nasal tube 16 during assembly or disassembly of the apparatus 10.

The air opening 36 and air passageway 34 are preferably of the same cross section or diameter as the lumen 28 of the nasal tube 16. As a result, air is permitted to flow freely through the air opening 36 of the aerosol-dispensing device with negligible air pressure drop through the air opening 36. During inhalation through the apparatus 10 air travels inwardly from the air (inlet) opening 36 through the air passageway 34 and lumen 28 into the nasal-pharyngeal cavity 32 and lungs 12 of the animal 14.

In testing an apparatus 10 substantially as described above by discharging four single shot doses of epinephrine bitartrate sold under the trademark "MEDIHALER-EPI" by Riker Laboratories, Inc. of St. Paul, Minnesota, U.S.A., approximately 95 percent of the discharge was found to consist of particle diameters of 6 micrometers or less, which is an optimum range for widespread lung deposition. The respirable mass in this test was approximately 9.2mg/$m^3$, and the mass median aerodynamic diameter was approximately 1.87 micrometers. The nasal tube 16 that was tested had an inside diameter of approximately 9 mm, an outside diameter of approximately 12.2 mm and a length L of approximately 350 mm. These results are believed to demonstrate that the apparatus 10 can generate an aerosol having a desired respirable mass and particle size for a broad pulmonary deposition pattern, which will facilitate rapid uptake of the drug into systemic circulation.

The apparatus 10 as described above has also been tested ex-vivo using an excised and isolated horse trachea 64 (FIG. 6) having a length of approximately 27 in. (690 mm). The excised trachea 64 was placed in an orientation approximately the same as it would be in the horse (i.e., at about 45 degrees from horizontal), and the distal end 26 of the nasal tube was placed adjacent the upper (open) end 66 of the trachea 64 before discharging an aerosol dose. Six locations 71-76 are identified in FIG. 6 where the various bronchi were sampled for drug content. Two trials were conducted, and the percentage of discharged drug that traversed the length of the trachea 64 and would be available for dispersion into the bronchi of the lobes of the horse lung 12 were calculated. The results are shown in the following table:

| Location | Trial 1 (mg/m$^3$) | Trial 2 (mg/m$^3$) | Mean | Relative Delivery (%) |
| --- | --- | --- | --- | --- |
| 71 | 13.8 | 14.4 | 14.1 | 27 |
| 72 | 9.4 | 15.0 | 12.2 | 23 |
| 73 | 11.9 | 13.1 | 12.5 | 24 |
| 74 | 1.9 | 1.6 | 1.8 | 3 |
| 75 | 13.7 | 9.2 | 11.5 | 22 |
| 76 | 1.1 | 0.7 | 0.9 | 2 |

In the event that it is desired to treat an animal that is unable to breath strongly enough to draw sufficient air through the nasal tube 16 for delivery of the aerosol dose, a pressurizing means (not shown) may be operatively mounted adjacent the air opening 36 of the device 18. For example, a suitable pressurizing means includes a collapsible bag (not shown) connected to the air opening 36 of the device 18. In order to increase inward (inspiratory) air flow the bag would be compressed.

A suitable alternative apparatus (not shown) that may be employed in performing the method of the invention is described in our coassigned U.S. Pat. Application, Ser. No. 07/460,315, entitled "Method of and Apparatus for the Aerosol Administration of Medication", filed Jan. 3, 1990, and hereby incorporated by reference. In that apparatus, the endotracheal or endotracheal-like tube includes a separate medication lumen having an orifice or nozzle adjacent the distal end of the endotracheal-like tube for discharging and atomizing the metered dose into the air stream.

In order to administer a drug via the apparatus 10, the nasal tube 16 is connected to the mounting section 58 of the aerosol-generating device 18, and the horse's head (also 14) may be secured using standard techniques commonly employed for passing nasal-gastric tubes. The distal end 26 of the nasal tube 16 is inserted through a nostril and nasal cavity of the large animal 14. The nasal tube 16 is inserted until the distal end 26 of the nasal tube 16 is positioned within the nasal-pharyngeal cavity 32 of the animal 14, with the lumen 28 of the nasal tube 16 communicating through the trachea with the lungs 12 of the animal 14.

An atomized aerosol drug dose is then discharged from the canister 22 into the lumen 28 of the nasal tube 16 when/as air flows inwardly through the lumen 28 of the nasal tube 16 toward the lungs 12.

It has been found that the nasal tube 16 can actually be inserted in this manner while the horse 14 is not sedated, with the horse 14 tolerating both the insertion of the nasal tube 16 and the discharge of the drug into its airway.

In order to optimize delivery of the atomized drug dose to the lungs 12 of the large animal 14, air flow through the lumen 28 of the nasal tube 16 is preferably determined so that the atomized drug may be discharged during the onset of inspiratory air flow through the lumen 28 toward the lungs 12. For example, the onset of inspiratory air flow may be determined by observing movement of the vane 56, or listening for the sound produced by the vane 56 striking the walls of the air passageway 34. Alternatively, U.S. Pat. No. 4,664,107 (incorporated herein by reference) describes a mechanism for ensuring that the canister 22 is only discharged at the appropriate time.

This method has been found to be particularly efficacious for treating recurrent airway obstruction or heaves in ponies. By administering an aerosol bronchodilator drug, such as a beta-2 bronchodilator drug (e.g., pirbuterol acetate, which is sold in an aerosol formulation under the trademark "MAXAIR" inhaler by Riker Laboratories, Inc. of St. Paul, Minnesota, U.S.A.) to ponies via the apparatus 10, heaves is readily treated.

As various changes could be made in the above constructions and methods without departing from the scope of the invention, it is intended that all matter contained in the above description or shown in the accompanying drawing be interpreted as illustrative and not in a limiting sense.

We claim:

1. A method of delivering a dose of an aerosol drug through the nasal-pharyngeal cavity of a large animal, such as a horse, for administration through its trachea to its lungs, the method comprising the following steps:
   inserting a distal end of an endotracheal-like nasal tube through a nostril and nasal cavity of the large animal until the distal end of the nasal tube is positioned within the nasal-pharyngeal cavity of the animal such that a lumen of the nasal tube communicates through the trachea with the lungs of the large animal; and
   discharging an aerosol drug dose into the lumen of the nasal tube when air flows inwardly through the lumen of the nasal tube toward the lungs for delivery of the drug dose to the lungs of the large animal.

2. A method according to claim 1 wherein the step of discharging an aerosol dose includes the steps of determining air flow through the lumen of the nasal tube, and discharging the drug dose generally during the onset of inspiratory air flow through the lumen of the nasal tube toward the lungs of the large animal.

3. A method according to claim 1 wherein the step of discharging an aerosol drug dose includes the step of discharging an aerosol bronchodilator drug into the lumen of the nasal tube for administration to the lungs of the large animal.

4. A method according to claim 1 wherein the step of inserting a distal end of a nasal tube includes inserting the distal end of the nasal tube through a nostril and nasal cavity of the large animal when the large animal is unsedated.

5. A method of delivering a dose of an aerosol drug through the nasal-pharyngeal cavity of a large animal, such as a horse, for administration through its trachea to its lungs, the method comprising the following steps:
   inserting a distal end of an endotracheal-like nasal tube through a nostril and nasal cavity of the large animal until the distal end of the nasal tube is positioned within the nasal-pharyngeal cavity of the animal such that a lumen of the nasal tube communicates through the trachea with the lungs of the large animal;
   discharging an aerosol drug dose into the lumen of the nasal tube when air flows inwardly through the lumen of the nasal tube toward the lungs for delivery of the drug dose to he lungs of the large animal;

wherein the step of discharging an aerosol drug dose includes the steps of determining air flow through the lumen of the nasal tube, and discharging the drug dose generally during the onset of inspiratory air flow through the lumen of the nasal tube toward the lungs of the large animal; and wherein the step of determining air flow through the lumen of the nasal tube comprises the steps of providing an air flow indicator including a vane movable in response to air flow through the lumen of the nasal tube, and determining the onset of air flow through the lumen by observing movement of the vane.

6. A method of delivering a dose of an aerosol drug to the lungs of a large animal, such as a horse, the method comprising the following steps:

providing an endotracheal-like nasal tube of the type having proximal and distal ends, and a lumen extending between the proximal and distal ends through which gas may flow, the nasal tube having a length appropriate for inserting the distal end thereof through a nostril into the nasal-pharyngeal cavity of the large animal;

providing an aerosol-generating device at the proximal end of the nasal tube with an air passageway of the device communicating with the lumen of the nasal tube to permit air flow into the proximal end of the nasal tube, the aerosol-generating device being of the type for dispensing aerosol into the air passageway of the device from a canister used for dispensing a metered dose of a drug through a hollow stem when the stem is actuated;

inserting the distal end of the nasal tube through a nostril of the large animal into the nasal-pharyngeal cavity so that the air passageway of the aerosol-dispensing device communicates through the lumen of the nasal tube with the lungs of the large animal;

determining air flow through the air passageway of the aerosol-dispensing device; and discharging an aerosol drug dose from the aerosol-dispensing canister into the air passageway during inspiratory air flow through the air passageway for delivery of the drug dose to the lungs of the large animal.

7. A method according to claim 6 wherein the aerosol-dispersing device includes an air inlet and outlet at opposite ends of the air passageway of the device, and tube-connecting means adapted for connecting the nasal tube to the device adjacent the air outlet of the device; the step of providing an aerosol-dispensing device at the proximal end of the nasal tube including connecting the nasal tube to the tube-connecting means of the aerosol-dispensing device, the method further comprising the step of freely permitting air flow through the air inlet of the aerosol-dispensing device with negligible air pressure drop through the air inlet.

8. A method according to claim 6 for use in farm animals to treat heaves, wherein the step of discharging an aerosol drug dose includes discharging an aerosol bronchodilator drug for administration to the lungs of the farm animal.

9. A method according to claim 6 wherein the step of inserting a distal end of a nasal tube includes inserting the distal end of the nasal tube when the large animal is unsedated.

10. A method according to claim 9 wherein the step of discharging an aerosol drug dose includes discharging the aerosol drug dose into a proximal end of the nasal tube.

11. A method of delivering a dose of an aerosol drug to the lungs of a large animal, such as a horse, the method comprising the following steps:

providing an endotracheal-like nasal tube of the type having proximal and distal ends, and a lumen extending between the proximal and distal ends through which gas may flow, the nasal tube having a length appropriate for inserting the distal end thereof through a nostril into the nasal-pharyngeal cavity of the large animal;

providing an aerosol-generating device at the proximal end of the nasal tube with an air passageway of the device communicating with the lumen of the nasal tube to permit air flow into the proximal end of the nasal tube, the aerosol-generating device being of the type for dispensing aerosol into the air passageway of the device from a canister used for dispensing a metered dose of a drug through a hollow stem when the stem is actuated;

inserting the distal end of the nasal tube through a nostril of the large animal into the nasal-pharyngeal cavity so that the air passageway of the aerosol-dispensing device communicates through the lumen of the nasal tube with the lungs of the large animal;

positioning the distal end of of said nasal tube in the animal's nasal-pharyngeal cavity, determining air flow through the air passageway of the aerosol-dispensing device;

discharging an aerosol drug dose from the aerosol-dispensing canister into the air passageway during inspiratory air flow through the air passageway for delivery of the drug dose to the lungs of the large animal;

wherein the aerosol-dispensing device includes an air inlet and outlet at opposite ends of the air passageway of the device, and tube-connecting means adapted for connecting the nasal tube to the device adjacent the air outlet of the device; the step of providing an aerosol-dispensing device at the proximal end of the nasal tube including connecting the nasal tube to the tube-connecting means of the aerosol-dispensing device, the method further comprising the step of freely permitting air flow through the air inlet of the aerosol-dispensing device with negligible air pressure drop through the air inlet; and wherein the step of determining air flow through the air passageway of the aerosol-dispensing device comprises the steps of providing an air flow indicator including a vane movable in response to air flow through the air passageway of the aerosol-dispensing device, and determining the onset of inspiratory air flow through the air passageway by observing movement of the vane.

12. A method according to claim 11 wherein the step of discharging an aerosol drug dose includes the step of discharging an aerosol bronchodilator drug into the air passageway for administration to the lungs of the large animal.

13. A method according to claim 12 wherein the step of discharging an aerosol bronchodilator drug includes discharging a beta-2 bronchodilator drug for administration to the lungs of the large animal.

14. A method according to claim 13 for use in preventing pulmonary hemorrhage in a horse prior to strenuous exercise, such as racing, wherein the step of discharging an aerosol bronchodilator includes discharging pirbuterol acetate for administration to the lungs of the horse.

15. Apparatus for administering a dose of an aerosol drug to the lungs of a large animal, such as a horse, the apparatus being adapted for use with a canister of the type for dispensing a metered dose of a drug through a hollow stem when the stem is actuated, the apparatus comprising:

an endotracheal-like nasal tube having proximal and distal ends, and a lumen extending between the proximal and distal ends, the nasal tube having a length and width appropriate for insertion of the distal end of the nasal tube through a nostril and nasal cavity of the large animal into the nasal-pharyngeal cavity of the large animal; and an aerosol-generating device mounted on the proximal end of the nasal tube, the device comprising a body having an air passageway communicating with the lumen of the nasal tube and an air opening opposite the nasal tube, the body including:

a stem receptacle outside and generally adjacent the air passageway for receiving the stem of the canister such that the stem is moved toward the canister when the canister is pushed toward the stem receptacle so that the stem may be actuated; and a hollow tube communicating with a hollow stem in the stem receptacle and extending generally transversely across the air passageway, the hollow tube having an orifice opening into the air passageway for delivering a metered aerosol dose to the air passageway for administration through the nasal tube to the lungs of the large animal.

16. Apparatus according to claim 15 further comprising an air flow indicator mounted in the air passageway of the body including a vane movable in response to air flow through the lumen of the nasal tube and adapted to generate an visible or audible signal when moved.

17. Apparatus according to claim 16 wherein the nasal tube is generally cylindrical, the nasal tube having an inner diameter of approximately 9 mm and an outer diameter of approximately 12 mm, and the length of the nasal tube being approximately 350 mm.

18. Apparatus according to claim 17 wherein the hollow tube comprises a narrow stainless steel tube having an outside diameter of approximately 1.2 mm and an inside diameter appropriate for preventing premature atomization of a metered dose inside the hollow tube, the orifice of the hollow tube opening through the hollow tube along the central longitudinal axis of the air passageway in the direction toward toward the nasal tube, the aerosol-dispensing device further comprising a canister housing detachably mountable on the body of the device including a triggering mechanism for moving the canister toward the stem receptacle, thereby moving the stem toward the canister to discharge an aerosol dose into the hollow tube.

19. Apparatus according to claim 18 further comprising a collapsible bag in fluid communication with the air opening of the aerosol-generating device for increasing inspiratory air flow through the air passageway of the device and nasal tube.

20. Apparatus according to claim 15 further comprises an air flow indicator for measuring the velocity of air flow through the air passageway, the air flow indicator including a tapered passageway in fluid communication with the air passageway, a float ball in the tapered passageway movable in response to the velocity of air through the air passageway, and a window in the body of the aerosol-generating device along the tapered passageway so that the float ball may be viewed.

* * * * *